United States Patent [19]

Stenzel et al.

[11] 4,409,231
[45] Oct. 11, 1983

[54] SUBSTITUTED ARYLOXYAMINO PROPANOLS, AND PROCESS FOR THEIR USE

[75] Inventors: Wolfgang Stenzel; Erich Cohnen, both of Hamburg, Fed. Rep. of Germany

[73] Assignee: Beiersdorf Aktiengesellschaft, Hamburg, Fed. Rep. of Germany

[21] Appl. No.: 164,214

[22] Filed: Jun. 30, 1980

[30] Foreign Application Priority Data

Jun. 30, 1979 [DE] Fed. Rep. of Germany ....... 2926517

[51] Int. Cl.³ .................. A01N 31/415; A01N 31/42; C07D 263/32; C07D 231/12
[52] U.S. Cl. .............................. 424/272; 424/273 P; 548/247; 548/378
[58] Field of Search .............................. 548/247, 378; 424/273 P, 272

[56] References Cited

U.S. PATENT DOCUMENTS 3,920,691 11/1975 Wasson et al. .................. 424/273 P
4,088,764 5/1978 Raabe et al. .................... 424/273 P
4,115,409 9/1978 Large et al. ........................ 548/378

OTHER PUBLICATIONS

Shionogi & Co. Ltd., "Chem. Abs.", vol. 96, (19), 162685m, (1982), Abstract of Japanese Kokai, 82/24375.
Stenzet et al., "Chem. Abs.", vol. 94, (25), 208858j, Abstract of German Offen DE 2, 926517, 1/15/81.
Richter, "Textbook of Organic Chemistry," 3rd. edition, 1952, p. 246.

Primary Examiner—Anton H. Sutto
Attorney, Agent, or Firm—Jordan B. Bierman; Linda Bierman

[57] ABSTRACT

Substituted aryloxyamino propanols and pharmaceutically acceptable acid addition salts thereof according to the following formula

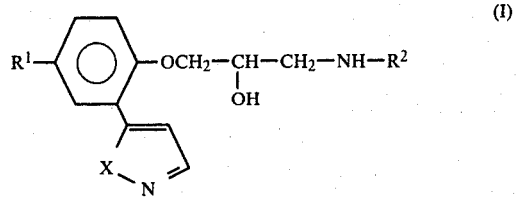

wherein X is selected from oxygen and NH, $R^1$ is selected from hydrogen, amino and acylamino having 1 to 8 carbon atoms, $R^2$ is selected from isopropyl, tertiarybutyl, and 2-(3,4-dimethoxyphenethyl), are disclosed which are useful as anti-hypertensive and β-adrenolytic agents. Also, substituted aryl azoles selected from 3-aryl pyrazoles and 5-aryl oxazoles having the formula

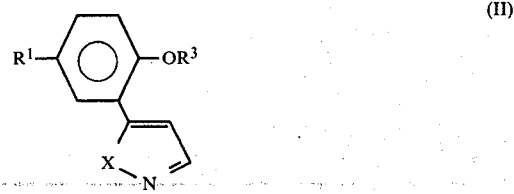

wherein X and $R^1$ are the same, and $R^3$ is selected from hydrogen, the radical

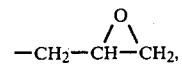

are disclosed which are useful in the preparation of the substituted aryloxyamino propanols of Formula I. Compositions containing the aryloxyamino propanols, and methods of preparation are also disclosed.

9 Claims, No Drawings

SUBSTITUTED ARYLOXYAMINO PROPANOLS, AND PROCESS FOR THEIR USE

This application claims the priority of German patent application No. P 29 26 517.6 filed June 30, 1979.

BACKGROUND OF THE INVENTION

The invention relates to substituted aryloxyamino propanols and the pharmaceutically acceptable acid addition salts which are useful as β-adrenolytic and anti-hypertensive agents. Compositions containing said compounds, their method of use, and methods of preparation form a part of the present invention, along with novel substituted aryloxyamino propanols useful in the preparation of the substituted propanols defined by Formula I.

SUMMARY OF THE INVENTION

The substituted aryloxyamino propanols according to the present invention are represented by the following formula

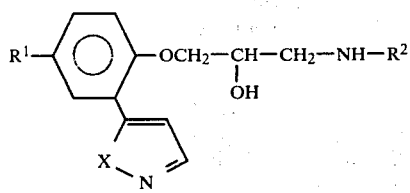

(I)

wherein X is selected from oxygen and an —NH— group, $R^1$ is selected from hydrogen, amino and acylamino having 1 to 8 carbon atoms, and $R^2$ is selected from isopropyl, tertiary-butyl, and 2-(3,4-dimethoxyphenethyl). When $R^1$ is acylamino, it may have the following formula

$R^4$—CONH— wherein $R^4$ is selected from hydrogen and alkyl having 1 to 7 carbon atoms, and aryl.

Particularly preferred substituted aryloxyamino propanols of the present invention are selected from 3-[5-acetamido-2-(2-hydroxy-3-tertiarybutylaminopropoxy)-phenyl]-pyrazole, 5-[5-butyramido-2-(2-hydroxy-3-isopropylamino-propoxy-phenyl]-isoxazole, 3-[5-amino-2-(2-hydroxy-3-isopropylamino-propoxy)-phenyl]-pyrazole, 3-[5-butyramido-2-(2-hydroxy-3-isopropylamino-propoxy)-phenyl]-pyrazole, 3-[2-(2-hydroxy-3-tertiarybutylamino-propoxy)-phenyl]-pyrazole, 3-[2-(2-hydroxy-3-[2-(3,4-dimethoxyphenethyl)] amino-propoxy)-phenyl]-pyrazole, 5-[2-(2-hydroxy-3-isopropylamino-propoxy)-phenyl]-isoxazole, 5-[2-(2-hydroxy-3-tertiarybutylamino-propoxy)-phenyl]-isoxazole, 3-[5-acetamido-2-(2-hydroxy-3-isopropylamino-propoxy)-phenyl]-pyrazole, 3-[5-acetamido-2-(2-hydroxy-3-[2-(3,4-dimethoxyphenethyl)] aminopropoxy)-phenyl]-pyrazole, 3-[5-propionamido-2-(2-hydroxy-3-isopropylamino-propoxy)-phenyl]-pyrazole, 5-[5-butyramido-2-(2-hydroxy-3-[2-(3,4-dimethoxyphenethyl)] amino-propoxy)-phenyl]-isoxazole, 3-[5-butyramido-2-(2-hydroxy-3-tertiarybutylamino-propoxy)-phenyl]-pyrazole, 3-[5-butyramido-2-(2-hydroxy-3-[2-(3,4-dimethoxyphenethyl)] amino-propoxy)-phenyl]-pyrazole and 3-[5-caproamido-2-(2-hydroxy-3-isopropyl-amino-propoxy)-phenyl]-pyrazole.

The compounds encompassed by Formula 1 are also useful in the form of acid addition salts. The salts can be prepared by reacting the compounds with suitable organic or inorganic acids. Preferred organic acids include oxalic acid, fumaric acid and maleic acid. Preferred inorganic acids include the halogen hydracids, such as, for example, HCl and HBr and sulfuric acid. Particularly, the compound and the desired acid are mixed and reacted in a solvent solution; and the solvent may, for example, comprise ether.

Compositions of the present compounds can be readily prepared by combining the compounds or the respective pharmaceutically acceptable acid addition salts with a pharmaceutically acceptable solid or liquid carrier. Particularly preferred carriers are selected from lactose, gelatin, corn starch, stearic acid, ethanol, propylene glycol, ethers of tetrahydrofurfuryl alcohol and water.

The compounds and compositions presently contemplated may be administered to a warm blooded animal in the form of solutions for injection. Particularly preferred is peroral administration in the form of dragees, pills, tablets or liquids. Peroral administration for humans may range in dosage from 50 to 500 mg per day, and preferably from about 250 to 350 mg per day. The present compounds and compositions exhibit β-adrenolytic and blood pressure-lowering action and can be employed for the treatment of angina pectoris, hypertonia and arrhythmia.

The present invention also relates to substituted aryl azoles comprising 3-aryl pyrazoles and 5-aryl oxazoles represented generally by the formula

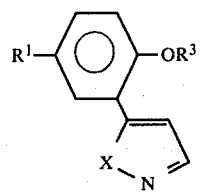

(II)

wherein X is selected from oxygen and an NH group, $R^1$ is selected from hydrogen, amino groups and acylamino groups having 1 to 8 carbon atoms, and $R^3$ is selected from hydrogen and the radical

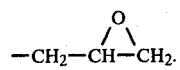

As with the compound of Formula 1, $R^1$ may also be selected from an acylamino group of the formula

$R^4$—CONH— wherein $R^4$ is selected from hydrogen and alkyl having 1 to 7 carbon atoms and aryl. When the compound of Formula II is prepared wherein $R^3$ is either the radical

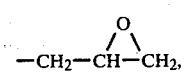

or hydrogen, the compounds are formed which are represented by the following formulas.

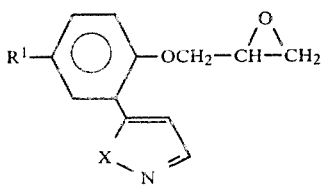

(III)

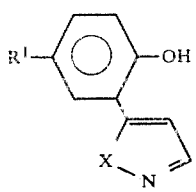

(IV)

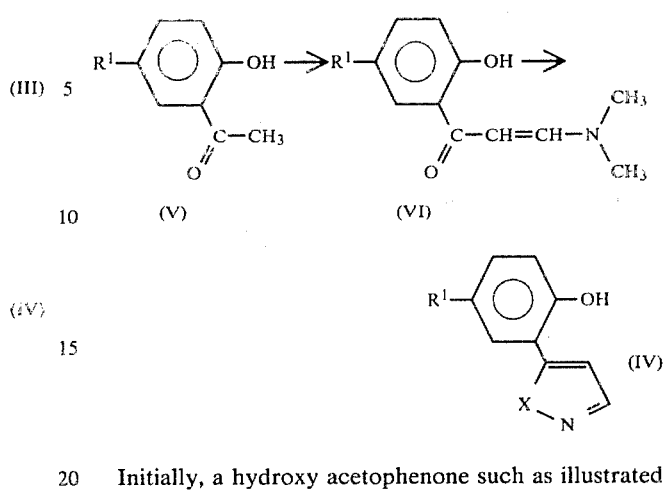

wherein X and R¹ are as previously described with reference to Formula II.

The compounds of Formulas III and IV are useful in the method of preparing the compounds of Formula I. Specifically, the compound of Formula III is reacted with an amine of the formula R²—NH₂, wherein R² is as described in Formula I. An excess of the amine reactant is preferably employed, and the reaction is carried out in the presence of an alcohol such as methanol, and at an elevated temperature ranging up to the boiling point of the reaction mixture. Preferably, the reaction is conducted under reflux at a boiling point of the reaction mixture for up to as long as 3 hours. After isolation, the resulting product may be converted to the acid salt by treatment with an ether solution of one of the acids stated earlier as suitable for this purpose.

In particular, the substituted aryl azoles of the present invention defined generally by Formula II are selected from 3-(5-acetamido-2-hydroxyphenyl)-pyrazole, 5-(5-butyramido-2-hydroxy-phenyl)-isoxazole, 3-(5-propionamido-2-hydroxyphenyl)-pyrazole, 3-(5-butyramido-2-hydroxyphenyl)-pyrazole, and 3-(5-caproamido-2-hydroxyphenyl)-pyrazole.

As noted earlier, the compounds according to Formula II have utility in the preparation of the compounds described in Formula I. Particularly, the compounds of Formula III are directly reacted as described earlier, and participate in the final step of the preparation of the compounds of Formula I. In turn, the compounds of Formula III are prepared by reacting the compounds of Formula IV with an epihalohydrin such as epichlorohydrin and epibromohydrin, in the presence of sodium hydroxide. Preferably, this reaction takes place in an aqueous solution at room temperature. The reaction mixture is agitated, as by stirring, and the reaction may be conducted for up to about 24 hours.

The compounds of Formula IV wherein R¹ is as previously described in Formula I can be prepared according to the method described below. The method is schematically illustrated as follows.

Initially, a hydroxy acetophenone such as illustrated by the Formula V is reacted with an excess of dimethyl formamide alkyl acetal, at a temperature ranging between room temperature and the boiling temperature of the reaction mixture. The reaction preferably proceeds under stirring for a period of time such as 2 hours, and may be held at a temperature of 50° C. The reaction yields a dimethylamino propenone represented by the Formula VI.

The second step in the method comprises the cyclization of the dimethylamino propenone to form the compound of Formula IV. In the instance where the pyrazole is desired, the propenone is reacted with hydrazine in a lower alcohol solvent, such as, for example, ethanol, and at a temperature ranging from room temperature to a maximum of the boiling temperature of the mixture. Preferably, the reaction mixture is heated for a period of time ranging up to about 2 hours, and at a temperature such as 50° C.

In the instance where the isoxazole derivative of the compound of Formula IV is desired, the propenone is cyclized with hydroxylamine hydrochloride, and a solvent comprising a dioxane-water mixture, in which both the propenone and the hydroxylamine hydrochloride are soluble. The reaction mixture is preferably stirred for a period of time ranging up to about 8 to 10 hours, during which time it may be maintained at room temperature. The reaction mixture is then diluted with water, alkalized, extracted with chloroform and acidulated to recover the isoxazole product.

The acetaphenones comprising the starting compound of Formula V are generally available and may be prepared by known methods described in the literature.

As noted earlier, the compounds of the present invention may be prepared wherein R¹ comprises an acylamino group of the formula R⁴—CONH—, with R⁴ selected from hydrogen and alkyl having 1 to 7 carbon atoms and aryl. These compounds may be prepared by a method which comprises an alternate embodiment of the present invention. Specifically, compounds of Formula IV where R¹ is —NH₂, may be reacted by a selective N-acylation, to convert the amino group to acylamino. The acylation agents useful in this method include acid anhydrides and acid chlorides carrying the desired acyl radical. The acylation agents are disposed in suitable solvents, such as, for example, a mixture of glacial acetic acid and water. The reaction is conducted at a temperature ranging up to about 100° C., and may be maintained under slight agitation by stirring for a period of time of up to about 24 hours. In this way, for example, formyl, acetyl, propionyl or butyrl groups, as well as aromatic substituents, may be introduced to the $R^1$ position. Also, the acylated amines of Formula IV obtained by this method may then be further reacted as described earlier to form the corresponding acyl compounds of Formula I.

In a further embodiment of this additional process, the compounds of Formula I wherein $R^1$ and $R^4$ are as stated above, may also be selectively acylated. In this instance, compounds of Formula I wherein $R^1$ is an amino group, can be prepared by acid hydrolysis of either the N-acetyl or N-acyl derivative of the compound. For example, acid hydrolysis is conducted by heating the substituted compound of Formula I with hydrochloric acid for a period of time such as 2 hours, after which the reaction product is concentrated and recovered in the known manner.

The following examples are for illustrative purposes only and are not meant to limit or in any way redefine the invention set forth in the broadest claim of the application.

EXAMPLE 1

3-[5-acetamido-2-(2-hydroxy-3-tertiarybutylamino-propoxy)-phenyl] pyrazole

A. 50 grams of 5-acetamido-2-hydroxyacetophenone were stirred with 200 grams of dimethylformamide dimethyl acetal, for 2 hours at a temperature of 50° C. The reaction mixture was then allowed to cool, and was suction-filtered to recover the crystals of reaction product that had formed. The crystals were then triturated with ether, and 58 grams of 3-dimethylamino-1-(5-acetamido-2-hydroxyphenyl)-2-propene-1-one were recovered. M.P.: 200° C.

B. 24 grams of the above propene-1-one were combined with 200 ml of ethanol and 33.5 ml of hydrazine hydrate, and the resulting mixture was heated for 2 hours at a temperature of 50° C. The mixture was then diluted with water, and the reaction product was extracted with chloroform, and thereafter subjected to evaporation. The resulting residue was then dissolved in ethylacetate, after which it was filtered. The filtrate was then reacted with petroleum ether until the start of crystallization; and 9.6 grams of 3-(5-acetamido-2-hydroxyphenyl)-pyrazole were finally recovered.

M.P.: 175° C.

C. 8 grams of the pyrazole prepared above were dissolved in a solution of 1.6 grams of NAOH in 80 ml of water. This solution was combined and reacted with 10 ml of epichlorhydrin, and was stirred for a period of 24 hours. The reaction product, comprising the epoxy pyrazole was recovered by extracting the reaction mixture with chloroform, and subsequently concentrating the extract. 5.2 grams of the epoxy compound was recovered in the form of oil.

The oil was then dissolved in 100 ml of methanol to which 6 ml of tertiarybutylamine was added. This mixture was then boiled with refluxing for 3 hours, after which it was subjected to evaporation under vacuum. The residue recovered from the evaporation was then taken up in dilute hydrochloric acid, and was thereafter extracted with chloroform. The solvent was thereafter drawn off, and the residue was purified by column chromatography conducted on a silica gel, and yielded 3-[5-acetamido-2-(2-hydroxy-3-tertiarybutylaminopropoxy)-phenyl]-pyrazole. The reaction product in the form of a free base was converted to the oxalate by reaction with an ether solution of oxalic acid. 1.5 grams of the oxalic acid addition salt was obtained.

M.P.: 205° C.

EXAMPLE 2

5-[5-butyramido-2-(2-hydroxy-3-isopropylamino-propoxy)-phenyl]-isoxazole.

A. 3-dimethylamino-1-(5-butyramido-2-hydroxy-phenyl)-2-propene-1-one was prepared from the corresponding acetephenone in the manner analogous to that of Example 1A. The product possessed a melting point of 174° C.

B. 9.5 grams of the propene-1-one prepared in paragraph A, above, were combined with 690 ml of dioxane, 170 ml of water and 2.4 grams of hydroxylamine hydrochloride. The resulting mixture was stirred overnight, after which it was diluted with 0.5 liters of water, and alkalized with potassium carbonate solution. The reaction product was then extracted with chloroform, after which it was acidulated with dilute hydrochloric acid to yield 5.2 grams of 5-(5-butyramido-2-hydroxy-phenyl)-isoxazole.

M.P.: 238° C.

C. The isoxazole product formed in paragraph B above was reacted in a manner analogous to that set forth in Example 1C and yielded 5-[5-butyramido-2-(2-hydroxy-3-isopropylamino-propoxy)-phenyl]-isoxazole in the form of a colorless oil.

EXAMPLE 3

3-[5-amino-2-(2-hydroxy-3-isopropylaminopropoxy)-phenyl]-pyrazole 10 grams of 3-[5-acetamido-2-(2-hydroxy-3-isopropylamino-propoxy)-phenyl]-pyrazole were heated with 150 ml of 2 n hydrochloric acid for a period of 2 hours. The reaction product was then concentrated to about 20% of the volume of the solution, and ethanol was added thereto, after which the resulting mixture was evaporated to dryness. The residue of evaporation was then triturated with ethylacetate and 6.2 grams of the desired aminopyrazole was obtained.

M.P.: 155°–158° C.

EXAMPLE 4

3-[5-butyramido-2-(2-hydroxy-3-isopropylamino-propoxy)-phenyl]-pyrazole 4 grams of the amino pyrazole prepared in Example 3, above, were combined with 4 grams of butyric acid anhydride in 1.5 ml of glacial acetic acid and 80 ml of water, and the resulting mixture was stirred and heated at 100° C. for a period of 24 hours. The resulting reaction product was then extracted with chloroform, and the organic phase of the solution was evaporated off. After evaporation was completed, the residue was triturated with ether dissolved in methanol, and was admixed with etheric oxalic acid. The oxalic acid addition salt of 3-[5-butyramido-2-(2-hydroxy-3-isopropylamino-propoxy)-phenyl]-pyrazole was recovered in a quantity of 1.2 grams.

M.P.: 140°–145° C.

EXAMPLES 5–15

In analogous manner to the procedures followed in Examples 1–4, compounds having the general structure of Formula I, set forth earlier, and substituted as set forth in Table 1, below, were prepared, and melting points where determined, were noted.

TABLE 1

| Example No. | R¹ | R² | X | M.P. °C. | Salt |
|---|---|---|---|---|---|
| 5 | H | t-butyl | NH | 155 | Oxalate |
| 6 | H | Y | NH | 128–130 | Oxalate |
| 7 | H | isopropyl | O | 135 | Oxalate |
| 8 | H | t-butyl | O | 175 | Oxalate |
| 9 | $CH_3-C(=O)-NH$ | isopropyl | NH | 159–162 | Oxalate |
| 10 | $CH_3-C(=O)-NH$ | Y | NH | 152 | Oxalate |
| 11 | $C_2H_5-C(=O)-NH$ | isopropyl | NH | 153 | — |
| 12 | $C_3H_7-C(=O)-NH$ | Y | O | 112 | — |
| 13 | $C_3H_7-C(=O)-NH$ | t-butyl | NH | 180 | Oxalate |
| 14 | $C_3H_7-C(=O)-NH$ | Y | NH | 115 | Oxalate |
| 15 | $C_5H_{11}-C(=O)-NH$ | isopropyl | NH | 170 | Oxalate |

What we claim is:

1. A compound of the formula

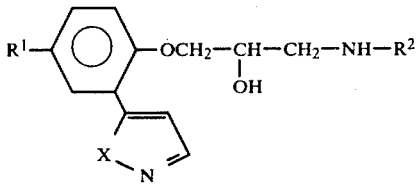

(I)

wherein X is selected from oxygen and an NH group, R¹ is selected from hydrogen, amino and acylamino having 1 to 8 carbon atoms, and R² is selected from isopropyl, tertiarybutyl, and 2-(3,4-dimethoxyphenethyl), and pharmaceutically acceptable acid addition salts thereof.

2. The compound of claim 1, wherein R¹ is an acylamino group of the formula R⁴—CONH— wherein R⁴ is selected from hydrogen and alkyl having 1 to 7 carbon atoms, and aryl.

3. The compound of claim 1 selected from the group consisting of 3-[5-acetamido-2-(2-hydroxy-3-tertiarybutylaminopropoxy)-phenyl]-pyrazole, 5-[5-butyramido-2-(2-hydroxy-3-isopropylamino-propoxy-phenyl]-isoxazole, 3-[5-amino-2-(2-hydroxy-3-isopropylamino-propoxy)-phenyl]-pyrazole, 3-[5-butyramido-2-(2-hydroxy-3-isopropylamino-propoxy)-phenyl]-pyrazole, 3-[2-(2-hydroxy-3-tertiarybutylamino-propoxy)-phenyl]-pyrazole, 3-[2-(2-hydroxy-3-[2-(3,4-dimethoxyphenethyl)] amino-propoxy)-phenyl]-pyrazole, 5-[2-(2-hydroxy-3-isopropylamino-propoxy)-phenyl]-isoxazole, 5-[2-(2-hydroxy-3-tertiarybutylamino-propoxy)-phenyl]-isoxazole, 3-[5-acetamido-2-(2-hydroxy-3-isopropylamino-propoxy)-phenyl]-pyrazole, 3-[5-acetamido-2-(2-hydroxy-3-[2-(3,4-dimethoxyphenethyl)] amino-propoxy)-phenyl]-pyrazole, 3-[5-propionamido-2-(2-hydroxy-3-isopropylamino-propoxy)-phenyl]-pyrazole, 5-[5-butyramido-2-(2-hydroxy-3-[2-(3,4-dimethoxyphenethyl)] amino-propoxy)-phenyl]-isoxazole, 3-[5-butyramido-2-(2-hydroxy-3-tertiary-butylamino-propoxy)-phenyl]-pyrazole, 3-[5-butyramido-2-(2-hydroxy-3-[2-(3,4-dimethoxyphenethyl)] amino-propoxy)-phenyl]-pyrazole and 3-[5-caproamido-2-(2-hydroxy-3-isopropylamino-propoxy)-phenyl]-pyrazole.

4. The compound of claim 1 wherein said salts are selected from the group consisting of maleinate, fumarate, oxalate, sulfate, hydrogen chloride and hydrogen bromide.

5. A composition comprising the compound of claim 1 in combination with a pharmaceutically acceptable carrier.

6. The composition of claim 5 wherein said carriers are selected from the group consisting of lactose, gelatin, cornstarch, stearic acid, ethanol, propylene glycol, ethers of tetrahydrofurfuryl alcohol, and water.

7. A method for lowering the blood pressure of a warm blooded animal comprising administering to said animal a therapeutically effective amount of the compound of claim 1.

8. The method of claim 6 wherein said therapeutically effective amount ranges from about 50 to 500 milligrams per day in the instance where said compound is administered to a human being.

9. The method of claim 8 wherein said therapeutically effective amount ranges from about 250 to 350 milligrams per day.

* * * * *